US008808317B2

(12) United States Patent
Braunagel

(10) Patent No.: US 8,808,317 B2
(45) Date of Patent: Aug. 19, 2014

(54) APPARATUS FOR CLEANING A NASAL CAVITY

(76) Inventor: Carl Braunagel, Cottonwood, AZ (US)

( * ) Notice: Subject to any disclaimer, the term of this patent is extended or adjusted under 35 U.S.C. 154(b) by 472 days.

(21) Appl. No.: 12/613,141

(22) Filed: Nov. 5, 2009

(65) Prior Publication Data
US 2010/0114071 A1   May 6, 2010

Related U.S. Application Data

(60) Provisional application No. 61/111,876, filed on Nov. 6, 2008.

(51) Int. Cl.
*A61M 3/00* (2006.01)
*A61M 3/02* (2006.01)

(52) U.S. Cl.
CPC ........... *A61M 3/0262* (2013.01); *A61M 3/0266* (2013.01); *A61M 3/0279* (2013.01); *A61M 2210/0618* (2013.01)
USPC .......................................... 606/162; 604/540

(58) Field of Classification Search
USPC ....................... 604/540; 606/162; 128/200.22
See application file for complete search history.

(56) References Cited

U.S. PATENT DOCUMENTS

| | | | | |
|---|---|---|---|---|
| 374,026 | A * | 11/1887 | Williams | 604/2 |
| 1,381,829 | A * | 6/1921 | Hartman | 606/162 |
| 1,466,474 | A * | 8/1923 | Hatcher et al. | 604/150 |
| 1,485,126 | A * | 2/1924 | Schumacher | 401/281 |
| 1,520,908 | A * | 12/1924 | Meyer | 606/162 |
| 1,599,787 | A * | 9/1926 | Perkiss | 604/217 |
| 1,658,801 | A * | 2/1928 | Condren | 606/162 |
| 1,681,320 | A * | 8/1928 | Bergl et al. | 604/145 |
| 2,024,723 | A * | 12/1935 | Dykema | 141/24 |
| 2,090,354 | A * | 8/1937 | Massman | 604/2 |
| 2,096,162 | A * | 10/1937 | Daley | 606/162 |
| 2,490,168 | A * | 12/1949 | Strauss | 604/2 |
| 2,520,605 | A * | 8/1950 | Maynier | 132/73 |
| 2,612,894 | A * | 10/1952 | Akins | 604/212 |
| 2,635,603 | A * | 4/1953 | Smith | 604/217 |
| 2,945,495 | A * | 7/1960 | Griffin | 604/257 |
| 3,797,481 | A * | 3/1974 | Doran | 601/155 |
| 3,903,888 | A * | 9/1975 | Buelow et al. | 604/186 |
| 4,012,798 | A * | 3/1977 | Liautaud | 4/620 |
| 4,256,107 | A * | 3/1981 | White | 604/248 |
| 4,258,714 | A * | 3/1981 | Leopoldi et al. | 604/118 |
| 4,329,990 | A * | 5/1982 | Sneider | 604/2 |
| 5,100,028 | A * | 3/1992 | Seifert | 222/107 |
| 5,110,013 | A * | 5/1992 | Clark et al. | 222/382 |
| 5,152,742 | A * | 10/1992 | Simpson | 604/3 |

(Continued)

FOREIGN PATENT DOCUMENTS

RU    2220710 C2 *  1/2004

*Primary Examiner* — Susan Su
(74) *Attorney, Agent, or Firm* — L.C. Begin & Associates, PLLC

(57) ABSTRACT

One embodiment of an apparatus for cleaning a nasal cavity includes a housing member and a hollow cleaning member. The housing member includes a first orifice, a second orifice and a chamber communicated with the first orifice and the second orifice. The chamber may be adapted to store fluid therein. The hollow cleaning member may be adapted to be received in the second orifice. The hollow cleaning member includes a head portion adapted to be received in the chamber of the housing member and a handle configured to fill the fluid from the chamber into the head portion. The head portion filled with the fluid is capable of cleaning the nasal cavity.

3 Claims, 3 Drawing Sheets

(56) References Cited

U.S. PATENT DOCUMENTS

| | | | |
|---|---|---|---|
| 5,269,684 A * | 12/1993 | Fischer | 433/90 |
| 5,312,009 A * | 5/1994 | Ratajczak et al. | 73/863.52 |
| 5,364,341 A * | 11/1994 | Cook | 604/30 |
| 5,400,923 A * | 3/1995 | Golias et al. | 222/82 |
| 5,464,048 A * | 11/1995 | Allen | 141/24 |
| 5,505,712 A * | 4/1996 | McMillian | 604/212 |
| 5,632,756 A * | 5/1997 | Kruglick | 606/162 |
| 5,715,850 A * | 2/1998 | Markgraaf | 132/333 |
| 5,816,804 A * | 10/1998 | Fischer | 433/90 |
| 5,857,991 A * | 1/1999 | Grothoff et al. | 604/2 |
| 5,895,408 A * | 4/1999 | Pagan | 606/199 |
| 5,899,878 A * | 5/1999 | Glassman | 604/48 |
| 5,921,233 A * | 7/1999 | Gold et al. | 128/200.22 |
| 5,947,986 A * | 9/1999 | Lewis | 606/161 |
| 6,074,405 A * | 6/2000 | Koch | 606/160 |
| 6,125,843 A * | 10/2000 | Gold et al. | 128/200.23 |
| 6,129,547 A * | 10/2000 | Cise et al. | 433/80 |
| 6,241,705 B1 * | 6/2001 | Ko-Wen | 604/73 |
| 6,270,510 B1 * | 8/2001 | Westendorf | 606/162 |
| 6,361,521 B1 * | 3/2002 | Erickson | 604/37 |
| 6,432,078 B1 * | 8/2002 | Peyman | 604/27 |
| 6,520,384 B2 * | 2/2003 | Mehta | 222/211 |
| 6,540,718 B1 * | 4/2003 | Wennek | 604/94.01 |
| 6,685,697 B1 * | 2/2004 | Arenberg et al. | 604/890.1 |
| 7,666,160 B2 * | 2/2010 | Rajala et al. | 604/13 |
| 2002/0099331 A1 * | 7/2002 | Burchfield | 604/94.01 |
| 2002/0169422 A1 * | 11/2002 | Ahnblad et al. | 604/217 |
| 2003/0109837 A1 * | 6/2003 | McBride-Sakal | 604/267 |
| 2003/0229306 A1 * | 12/2003 | Sherman | 604/93.01 |
| 2004/0054322 A1 * | 3/2004 | Vargas | 604/95.04 |
| 2006/0264851 A1 * | 11/2006 | Coleman | 604/279 |
| 2007/0265595 A1 * | 11/2007 | Miyamoto et al. | 604/528 |
| 2007/0276312 A1 * | 11/2007 | Davis et al. | 604/3 |
| 2009/0088678 A1 * | 4/2009 | Noda et al. | 604/8 |
| 2009/0112241 A1 * | 4/2009 | Bar et al. | 606/162 |
| 2011/0066172 A1 * | 3/2011 | Silverstein | 606/162 |
| 2011/0319840 A1 * | 12/2011 | Hair | 604/275 |
| 2012/0302957 A1 * | 11/2012 | Vlodaver et al. | 604/151 |

* cited by examiner

US 8,808,317 B2

APPARATUS FOR CLEANING A NASAL CAVITY

CROSS-REFERENCE TO RELATED APPLICATION

This application claims the benefit of U.S. Provisional Application Ser. No. 61/111,876 filed on Nov. 6, 2008, the disclosure of which is incorporated by reference.

FIELD OF THE DISCLOSURE

The present disclosure generally relates to cleaning apparatuses, and more particularly, to an apparatus for cleaning a nasal cavity.

BACKGROUND OF THE DISCLOSURE

A human nose has various defense mechanisms to prevent impurities from entering the body. A screen of hairs is present at the entrance to the nose, which traps dust particles, tiny insects and other particles. Further, the nose has a nasal cavity lined with a mucus membrane that helps to warm excessively cool air and also blocks very fine dust particles that pass through the hair screen. However, mucus may accumulate in the nasal cavity and block the same thereby leading to respiratory infections.

SUMMARY OF THE DISCLOSURE

One embodiment of an apparatus for cleaning a nasal cavity may include a housing member and a hollow cleaning member. The housing member may include a first orifice, a second orifice and a chamber communicated with the first orifice and the second orifice. The chamber may be adapted to store fluid therein. The hollow cleaning member may be adapted to be received in the second orifice. The hollow cleaning member may include a head portion adapted to be received in the chamber of the housing member and a handle configured to fill the fluid from the chamber into the head portion. The head portion filled with the fluid may be capable of cleaning the nasal cavity.

BRIEF DESCRIPTION OF THE DRAWINGS

The advantages and features of the present disclosure will become better understood with reference to the following detailed description and claims taken in conjunction with the accompanying drawings, wherein like elements are identified with like symbols, and in which:

Like reference numerals refer to like parts throughout the description of several views of the drawings.

DETAILED DESCRIPTION OF THE DISCLOSURE

The exemplary embodiments described herein provide detail for illustrative purposes only and are subject to many variations in structure and design. It should be emphasized, however, that the present disclosure is not limited to a particular apparatus for cleaning a nasal cavity, as shown and described. It is understood that various omissions and substitutions of equivalents are contemplated as circumstances may suggest or render expedient, but these are intended to cover the application or embodiment without departing from the spirit or scope of the claims of the present disclosure.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

The present disclosure provides an apparatus for cleaning a nasal cavity. The term "cleaning" as used herein relates to a process of sanitizing and/or removing contaminants, such as mucus, dust particles, tiny insects and other particles from the nasal cavity.

Figure 1:
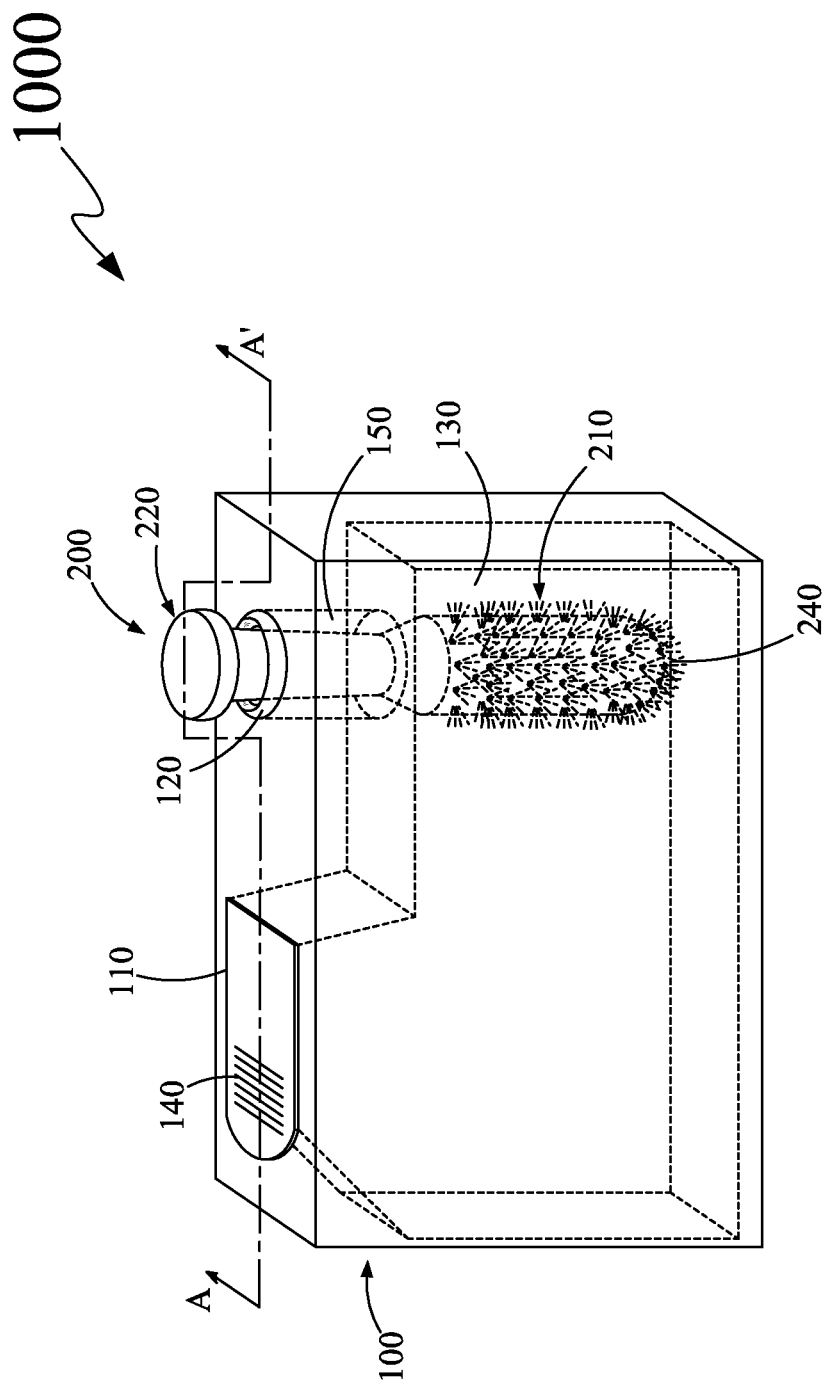
FIG. 1 is a perspective view of an embodiment of an apparatus for cleaning a nasal cavity.
Figure 2:
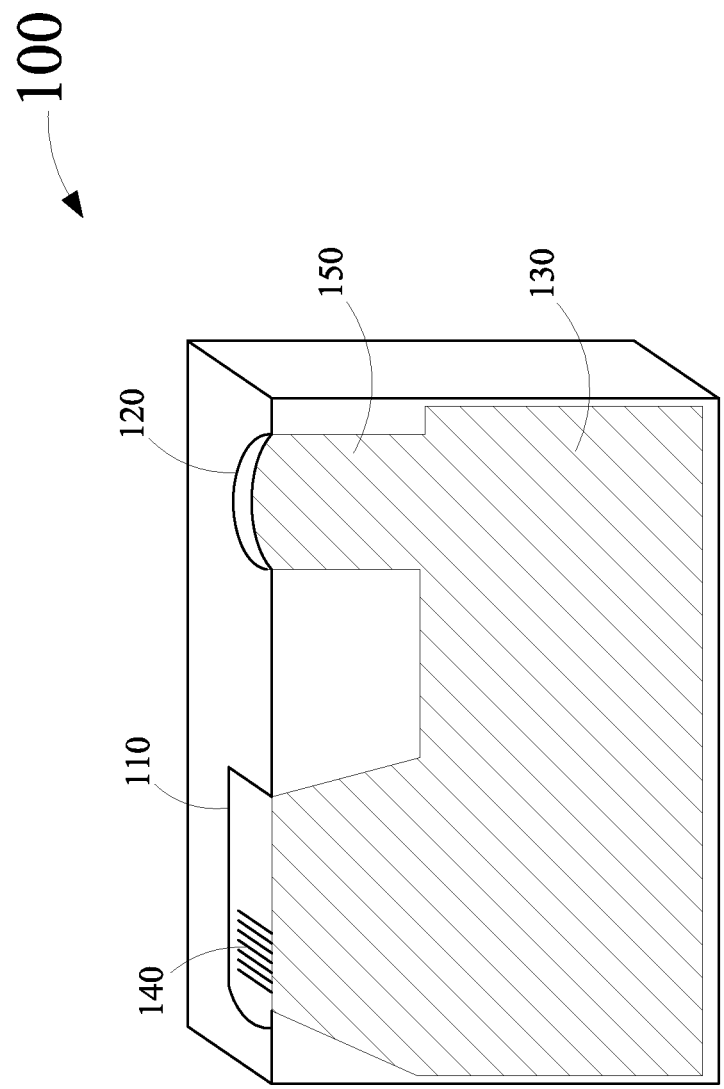
FIG. 2 is a cross sectional view of a housing member of the apparatus of FIG. 1.
Figure 3:
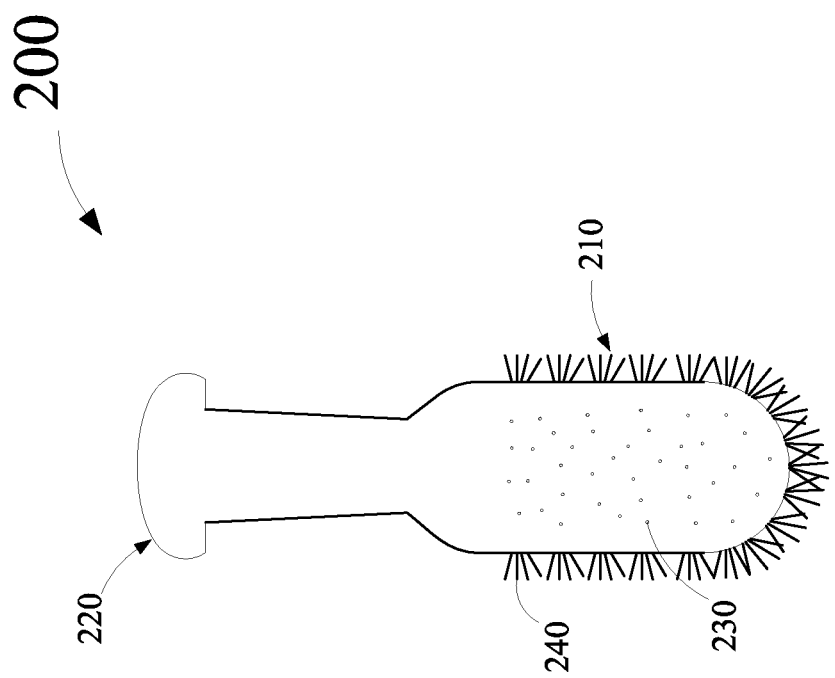
FIG. 3 is a cross sectional view of a hollow cleaning member of the apparatus of FIG. 1.

Referring to FIGS. 1-3, one embodiment of an apparatus 1000 for cleaning a nasal cavity (not shown) may include a housing member 100 having a cuboidal shape. Alternatively, the housing 100 may be configured to have various other shapes such as a cylindrical shape, a trapezoidal shape, a polygonal shape or any other suitable shape. The housing member 100 may include a first orifice 110, a second orifice 120 and a chamber 130 communicated with the first orifice 110 and the second orifice 120. The chamber 130 may be adapted to store a fluid (not shown). The fluid may be a mixture of pharmaceutical grade sodium chloride, sodium bicarbonate powder and water in specific quantities. Of course, the fluid may instead be a saline solution or other suitable fluids. The fluid acts a disinfectant and anti-bacterial fluid. Further, the first orifice 110 may have a slidable door 140 for closing and opening the first orifice 110. Also, the second orifice 120 may have a lining 150 extending from the second orifice 120 to the chamber 130. The fluid may be introduced into the chamber 130 through the first orifice 110.

Referring to FIGS. 1 and 3, the apparatus may also include a hollow cleaning member 200, which in one form may be an elongated structure having a head portion 210 and a handle 220. The head portion 210 may have a plurality of perforations 230. Further, the head portion 210 may include a plurality of projections 240. Each of the projections 240 may be a soft bristle like structure. The head portion 210 may be capable of being introduced into the nasal cavity (not shown). The handle 220 may be a bulb communicated with the interior of the head. The bulb may be made of an elastic material, such as rubber or other suitable elastic materials.

Further, the head portion 210 of the hollow cleaning member 200 may be inserted through the second orifice 120 of the housing member 100 thereby immersing the head portion 210 in the fluid contained in the chamber 130. The lining 150 of the housing member 100 may be adapted to secure the hollow cleaning member 200 in the housing member 100. Also, the handle 220 or bulb may be squeezed to force air from the hollow cleaning member 200 and then released to return the handle toward its original such that the a partial vacuum within the hollow cleaning member 200 may draw the fluid from the chamber 130 into the head portion 210.

In use, the fluid may be filled in the chamber 130 of the housing member 100 through the first orifice 110. After filling the chamber 130, the slidable door 140 may be moved in a manner such that the first orifice 110 may be closed. The hollow cleaning member 200 may be introduced in the second orifice 120 in a manner such that the head portion 210 may be immersed in the fluid contained in the chamber 130. The handle 220 may help to draw the fluid from the chamber 130 into the head portion 210 and fill the head portion 210. The fluid may enter into the head portion 210 through the plurality of perforations 230. The hollow cleaning member 200 filled with the fluid may be withdrawn from the housing member 100. Thereafter, the head portion 210 may be introduced into the nasal cavity of a user. The handle 220 may be worked upon to release the fluid filled in the head portion 210 into the nasal cavity. The fluid may be released into the nasal cavity through the plurality of perforations 230. The fluid may help to loosen the mucus, dust particles and other particles attached in the nasal cavity and also to disinfect the nasal cavity. Further the plurality of projections 240 may also help to loosen and remove the mucus, dust particles and other particles. The head portion 210 may be rotated in the nasal cavity with the help of the handle 220 in a manner such that every trace of the mucus, dust particles and other particles may stick to the plurality of projections for complete cleansing of the nasal cavity. After the fluid has been released into the nasal cavity and the mucus, dust particles and other particles have attached to the plurality of projections 240, the head portion 210 may removed from the nasal cavity and the hollow cleaning member 200 may be washed with the water. Likewise, the same procedure may be applied for cleaning the other nasal cavity.

The present disclosure provides an apparatus, such as the apparatus 1000 for cleaning the nasal cavity. The hollow cleaning member and the fluid utilized for cleaning the nasal cavity provides an easy way of removing the mucus, dust particles and other particles from the nasal cavity, thereby cleaning the nasal cavity. Accordingly, the apparatus prevents the accumulation of the mucus, dust particles and other particles in the nasal cavity and as such prevents infection of the nasal cavity.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, and to thereby enable others skilled in the art to best utilize the present disclosure and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the claims of the present disclosure.

What is claimed is:

1. An apparatus for cleaning a nasal cavity, the apparatus comprising:
    a housing member having an orifice and a chamber communicated with the orifice, the chamber adapted to store fluid therein; and
    a hollow cleaning member having a head portion adapted to be received in the chamber, the head portion including a plurality of perforations extending along a surface thereof and enabling fluid communication between an exterior of the head portion and an interior of the head portion,
    the head portion also including a plurality of bristle-like projections extending from an exterior of the head portion, the projections being interspersed between perforations of the plurality of perforations,
    the head portion being structured so as to provide direct contact between the at least one perforation and a fluid positioned in the chamber whenever the head portion is received in the chamber.

2. The apparatus of claim 1, wherein the fluid comprises a mixture of sodium chloride, sodium bicarbonate and water.

3. The apparatus of claim 1, further comprising another orifice in fluid communication with the orifice and with the chamber, wherein the other orifice is structured for receiving fluid therethrough into the chamber for storage.

* * * * *

UNITED STATES PATENT AND TRADEMARK OFFICE
CERTIFICATE OF CORRECTION

PATENT NO. : 8,808,317 B2  
APPLICATION NO. : 12/613141  
DATED : August 19, 2014  
INVENTOR(S) : Braunagel Page 1 of 1

It is certified that error appears in the above-identified patent and that said Letters Patent is hereby corrected as shown below:

In the Specification

Column 2; Line 55;   Please delete "the".

Signed and Sealed this  
Fourth Day of November, 2014

Michelle K. Lee  
*Deputy Director of the United States Patent and Trademark Office*